United States Patent [19]

Baret

[11] Patent Number: 5,108,893

[45] Date of Patent: Apr. 28, 1992

[54] USE OF OXIDASE ENZYME SYSTEMS IN CHEMILUMINESCENT ASSAYS

[75] Inventor: Alain Baret, Lafayette, France

[73] Assignee: Canberra Industries, Inc., Meriden, Conn.

[21] Appl. No.: 536,181

[22] Filed: Jun. 11, 1990

Related U.S. Application Data

[63] Continuation-in-part of Ser. No. 81,159, Aug. 4, 1987, Pat. No. 4,933,276.

[30] Foreign Application Priority Data

Aug. 6, 1986 [FR] France .................. 86 11415

[51] Int. Cl.$^5$ ............... C12Q 1/68; C12Q 1/26; C12Q 1/28
[52] U.S. Cl. ............................. 435/6; 435/25; 435/28; 435/810; 436/172; 252/700
[58] Field of Search ............ 252/700; 435/6, 25, 435/28, 810; 436/172, 904; 422/52

[56] References Cited

U.S. PATENT DOCUMENTS

| | | | |
|---|---|---|---|
| 4,235,869 | 11/1980 | Schwarzberg | 424/8 |
| 4,358,535 | 11/1982 | Falkow et al. | 435/5 |
| 4,363,759 | 12/1982 | Boguslaski et al. | 530/303 |
| 4,375,972 | 3/1983 | Forgione et al. | 436/531 |
| 4,376,825 | 3/1983 | Rubenstein et al. | 435/188 |
| 4,478,817 | 10/1984 | Campbell et al. | 424/7.1 |
| 4,563,417 | 1/1986 | Albarella et al. | 435/6 |
| 4,598,044 | 7/1986 | Kricka et al. | 435/28 |
| 4,604,364 | 8/1986 | Kosak | 436/501 |
| 4,617,261 | 10/1986 | Sheldon, III et al. | 435/6 |
| 4,629,690 | 12/1986 | Weng et al. | 435/7.91 |
| 4,794,073 | 12/1988 | Dattagupta et al. | 435/6 |

FOREIGN PATENT DOCUMENTS

| | | |
|---|---|---|
| 0016845 | 10/1980 | European Pat. Off. |
| 0175560 | 3/1986 | European Pat. Off. |
| 8503356 | 8/1985 | PCT Int'l Appl. |

OTHER PUBLICATIONS

Schroeder et al., "Chemiluminescence Yields and Detection Limits of Some Isoluminol Derivatives in Various Oxidation Systems", Analytical Chemistry, 50:1114-1120 (1978).

Chemical Abstracts 97:177149j (Nov. 1982).

Yaxley, "the Amerlite Enhanced Lumninescence Immunoassay System", pp. 1-13.

Winterbourn et al., "Iron and Xanthine Oxidase Catalyze Formation of an Oxidant Species Distinguishable from OH: Comparison with the Haber-Weis Reaction", Arch. Biochem. & Bioph., 244:27-34 (1986).

Kricka et al., "Luminescent Immunoassays: New labels for an established technique", Diagnostic Medicine, 44-52 (1984).

Hodgeson et al., "The Mechanism of the Activity-Dependent Luminescence of Xanthine Oxidase", Arch. Biochem. & Bioph., 172:202-205 (1976).

Wilhelm et al., "Variables in Xanthine Oxidase-Initiated Luminol Chemiluminescence: Implications for Chemiluminescence Measurements in Biological Systems", Analytical Biochemistry, 158:201-210 (1986).

Primary Examiner—Esther L. Kepplinger
Assistant Examiner—Susan C. Wolski
Attorney, Agent, or Firm—Arnold, White & Durkee

[57] ABSTRACT

A xanthine oxidase enzyme system to provide long lived entities capable of being recognized by a chemiluminescent reagent is disclosed. In the examples provided, a specific binding pair ligand or analyte is coupled with xanthine oxidase, either directly or via a streptavidin bridge. Thereafter, the presence of an analyte can be determined by a chemiluminescent emission upon addition of a signal reagent comprising hypoxanthine, iron EDTA complex and luminol dissolved in barbital buffer. The resulting chemiluminescent signal is stable and detectable for many hours after initiation. The chemiluminescent xanthine oxidase system is particularly useful for immunoassays and DNA probe analysis.

25 Claims, 8 Drawing Sheets

USE OF OXIDASE ENZYME SYSTEMS IN CHEMILUMINESCENT ASSAYS

BACKGROUND OF THE INVENTION

This application is a continuation-in-part of application Ser. No. 07/081,159, filed Aug. 4, 1987 (which claims benefit of a prior foreign filing made in France on Aug. 6, 1986, Ser. No. 86-11415) and issued as U.S. Pat. No. 4,933,276 on Jun. 12, 1990.

The present invention relates to the use of an xanthine oxidase (XO) enzyme reaction system in chemiluminescent assays, including immunoassays and DNA probe analysis.

The use of bioluminescence and chemiluminescence in immunoanalysis has been extended to many analytes (KINGLER, W., STRASBURGER C.J., and WOOD W.G., *Trends in Analytical Chemistry* 2:132-136, 1983; KRICKA L.J., and THORPE G.H.G., Analyst 08:1274-1296, 1983). Chemiluminescent assays generally fall into two categories:

(a) The quantifiable phenomenon consists of a very brief signal (a few seconds) obtained after instantaneous injection of triggering reagent into the reaction medium. Such is the case with assays using, as a tracer, coupling derivatives of luminol (SCHROEDER H.R., et al: *Methods Enzymology* 57:424-445, 1978) or of acridinium esters (WEEKS I. and WOODHEAD J.S. in *Analytical Applications of Bioluminescence and Chemiluminescence*, Academic Press, pp. 185-188, 1984). Apart from the disadvantage associated with the brevity of the signal, this procedure demands the use of an apparatus for injecting the reagents into the measuring chamber itself. In consequence, application to microtitration plates is difficult and relatively sophisticated and expensive apparatus is required for other detection vessels.

(b) The quantifiable phenomenon consists of a longer-lasting signal, which can be measured for a significant time period, enabling measurements to be repeated where appropriate and the samples to be prepared outside the luminometer. In such a system, an injection system is not required, thereby simplifying the design of the luminometer and allowing use of microtitration plates.

At present, only one procedure has been described in which a relatively stable and intense chemiluminescence signal is obtained. This procedure is based on enhancement of the peroxidase-dependent oxidation reaction of cyclic diacylhydrazides by compounds such as synthetic luciferin, 6-hydroxybenzothiazole derivatives or substituted phenols (para-iodophenol) [WHITEHEAD T.P., THORPE G.H.G., CARTER T.J.N. et al., *Nature* (London) 305:158-159, 1983; THORPE G.H.G., KRICKA L.J. et al., *Anal. Biochem.* 145:97-100, 1985; THORPE G.H.G., KRICKA L.J. et al., *Clin. Chem.* 31:1335-1341, 1985]. This method is currently applied to the assay of many analytes. However, it should be noted that the term and constancy of the signal is only relative, since the measurements can be performed only during some 30 or 40 minutes.

The use of xanthine oxidase in a light producing system has been previously contemplated by others, such as Boguslaski, U.S. Pat. No. 4,363,759 and Molecular Biosystem, Inc., WO-A-85 03,356. However, no evidence or parameters are described which result in a long duration signal. Furthermore, xanthine oxidase is listed together with many other enzyme systems which, as a whole, do not produce both $H_2O_2$ and superoxide anion radicals.

SUMMARY OF THE INVENTION

It has now been discovered that certain oxidase enzymes such as xanthine oxidase, choline oxidase, sarcosine oxidase and fumarate oxidase, which produce oxygen-containing free radicals (e.g., superoxide anion $O_2^-$ hydroxyl radical OH.) and peroxide ($H_2O_2$: hydrogen peroxide) provide long-lived chemiluminescent detectable products upon reaction with chemiluminescent reagents, such as lucigenin, luminol and its derivatives. These chemiluminescent products provide a signal which is very stable with time and measurable during periods of several hours, even up to several days; this stability and long duration is much greater than that of all the methods known at present.

The oxidase enzyme systems of the present invention are particularly useful as a tracer for detection of analytes in immunoassays, immunoblotting, or nucleotide probe analysis to provide long lived light emitting entities after reaction with a chemiluminescent reagent. In the context of this invention, these long-lived light emitting entities are stable for more than 20 hours, with most emitting light for 120 hours and more.

In general, the present chemiluminescent oxidase systems provide a tracer consisting of analyte or ligand coupled to the selected oxidase enzyme. This tracer can be detected by a chemiluminescent reaction upon the addition of a signal reagent. The signal reagent comprises an oxidase substrate; an enhancer, for instance a transition metal complex, particularly an iron complex; and a chemiluminescent reagent, dissolved in high ionic strength organic-based alkaline pH buffer, such as a barbital, borate or carbonate buffer, and a preferred pH range of about 9.5 to about 10.5.

The substrates which are associated with the oxidase enzyme systems are any of the substrates specific for the selected enzyme. For example, when xanthine oxidase is selected, the substrate associated with xanthine oxidase (XO) in this enzyme system includes hypoxanthine, xanthine, acetaldehyde or purine. Hypoxanthine is most especially preferred.

In the context of the present invention, the chemiluminescent reagent is selected from acridinium esters, lucigenin or its derivatives, or luminol or its derivatives. Luminol and its derivatives are 2,3-dihydro 1,4-phthalazinedione compounds, which have been defined in several previous patents, e.g., U.S. Pat. Nos. 4,598,044, 4,478,817 and 4,363,759. Acridinium esters, lucigenin and its derivatives have previously been defined in U.S. Pat. No. 4,478,817.

Further, the present invention features different methods of assay employing the subject chemiluminescent oxidase enzyme systems.

The chemiluminescent oxidase enzyme systems of this invention are particularly useful in the context of immunoenzymatic analytical procedures such as immunometric or competitive binding assays. Such immunoassay techniques are generally well known in the art. For example, David et al., U.S. Pat. No. 4,486,530, provides in its BACKGROUND OF THE INVENTION a discussion of various design techniques for enzyme linked immunoassays.

The present oxidase enzyme systems can also be employed in immunoassay procedures using the avidin-biotin system. (See *Laboratory Techniques in Biochemistry and Molecular Biology*, Vol. 15, Edited by R. H. Burdon et al. Elsevier Press.) In that case, a conjugate of enzyme-biotin takes advantage of the high affinity constant of the avidin-biotin interaction to obtain a stable biotinylated enzyme-avidin stable complex. This complex provides a universal tracer which can be used in both types of immuno analysis, immunometric and competitive. Indeed, it can be optimized to present free avidin sites (each molecule of avidin can fix four molecules of biotin), which can fix other biotinylated molecules.

Further, the chemiluminescent oxidase systems of the present invention are useful as a chemiluminescent detection system for nucleotide probe analysis. A general discussion for nucleotide probe hybridization techniques is given in Falkow et al., U.S. Pat. No. 4,358,535.

Thus, in general, the chemiluminescent oxidase systems of the present invention can be adapted for use in a wide variety of assays designed to detect an analyte wherein a specific binding pair ligand is coupled with an enzymatic or substrate tracer.

Consistent with the generally accepted terminology in the art and in the context of this disclosure, the following terms are defined:

As used herein, an analyte is a specific bindable material whose presence or amount is to be determined. Examples of analytes include antigens, haptens, antibodies, glycosylated proteins, carbohydrates and oligonucleotides.

As used herein, a ligand is a specific binding partner of the analyte, which has a specific binding affinity for the analyte to the exclusion of other substances. Examples of ligands include antibodies, lectins and oligonucleotides.

DETAILED DESCRIPTION OF THE PREFERRED EMBODIMENTS

Figure 2:
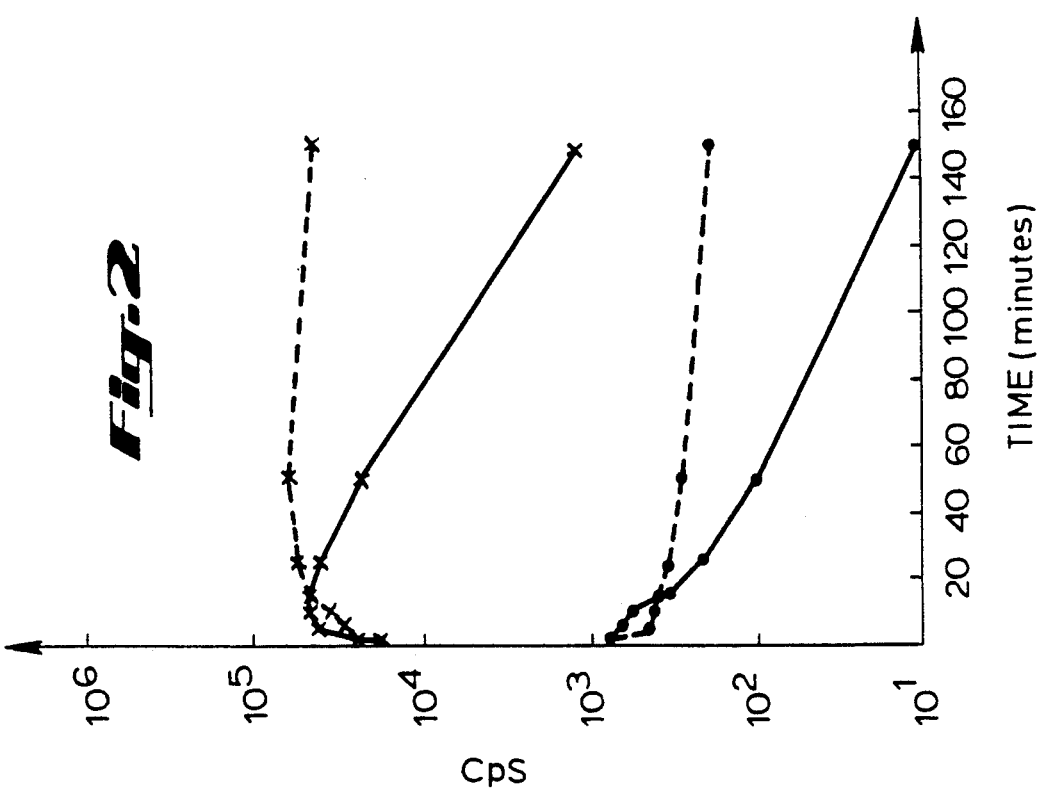

The following discussion is in terms of the preferred embodiments of this invention, which represent the best mode known to the Applicant at the time of this application.

The present invention is based on the realization that certain oxidases which produce both $H_2O_2$ and $O_2^-$, including, for example, xanthine oxidase, choline oxidase, fumarate oxidase and sarcosine oxidase, are capable of generating long-lived light emitting entities when reacted with an oxidase substrate, a chemiluminescent reagent and an enhancer under pH conditions ranging from about 9.5 to about 10.5.

Specific examples of design methodologies of using the chemiluminescent oxidase enzyme systems of the present invention include the following:

In a method for the detection of a hapten or antigen as the analyte, a competitive immunoassay can be employed comprising the steps of:
(a) providing a solid support such as a tube, microtiter well, or beads, deposited with a ligand such as a lectin or antibody specific for said analyte;
(b) providing a tracer consisting of an analyte coupled to an oxidase by direct covalent linkage or by an avidin bridge between biotinylated enzyme and biotinylated analyte;
(c) incubating the sample containing the analyte, antigen or hapten to be assayed in the presence of the solid support prepared in stage (a) and the tracer prepared in stage (b);
(d) washing the support;
(e) adding a signal reagent which includes a substrate associated with the oxidase, an enhancer and a chemiluminescent reagent, maintained at a pH ranging from about 9.5 to about 10.5; and
(f) measuring the chemiluminescent response and deducing the concentration of antigen or hapten from the measurement thereby performed.

The kit of reagents required for carrying out this method, which also forms the subject of the present invention, is characterized in that it contains:
(a) a solid support, such as a tube, microtiter plate, or beads, coated with ligand such as an antibody or lectin specific for the antigen or hapten analyte to be assayed;
(b) a product of coupling of the analyte and an oxidase; and
(c) a substrate associated with the oxidase, a chemiluminescent reagent, and an enhancer, all maintained at a pH ranging from about 9.5 to about 10.5.

In a method to detect an antigen or antibody as the analyte, an immunometric assay can be employed comprising the steps of:
(a) providing a solid support such as a tube, microtiter well, or beads, deposited with a ligand such as a lectin or antibody specific for said analyte;
(b) providing a tracer consisting of a complementary ligand coupled to an oxidase by direct covalent linkage or by an avidin bridge between biotinylated enzyme and biotinylated ligand;
(c) incubating a sample containing the analyte to be assayed in the presence of the solid support and the tracer;
(d) separating the unbound tracer from the bound tracer by washing the solid support;
(e) adding to the washed support a signal reagent comprising an oxidase substrate, a chemiluminescent reagent and an enhancer maintained at a pH ranging from about 9.5 to about 10.5; and
(f) measuring the chemiluminescent response and deducing the amount of the analyte in the sample.

A kit of reagents for carrying out an immunometric chemiluminescent assay of the present invention would include:
(a) a solid support, such as a tube, microtiter plate, or beads, coated with a ligand such as an antibody or ligand specific for the analyte to be assayed;
(b) a tracer consisting of a coupling product of an oxidase and a second ligand which is specific for the analyte to be assayed; and
(c) a signal reagent comprising an oxidase substrate, a chemiluminescent reagent, and an enhancer, all at a pH ranging from about 9.5 to about 10.5.

With respect to nucleotide probes hybridization techniques, the present chemiluminescent oxidase system can be used to detect a hybridized duplex formation as follows:
(a) depositing genetic material of an analyte to a solid support, such as a filter, tube or microtiter plate;
(b) incubating under hybridizing conditions a tracer consisting of an oligonucleotide probe coupled to an oxidase, the probe having a nucleotide sequence substantially complementary to the genetic material of the analyte;
(c) washing the support;
(d) adding a substrate associated with the oxidase, an enhancer and a chemiluminescent reagent under pH conditions ranging from about 9.5 to about 10.5; and (e) measuring the chemiluminescent response to determine the concentration or presence of the duplex formed.

A kit of reagents for carrying out this method includes:
(a) a solid support, such as a filter, tube or microtiter plate;
(b) an oligonucleotide probe coupled with an oxidase; and
(c) a substrate associated with the oxidase, a chemiluminescent reagent, and an enhancer, all maintained at a pH ranging from about 9.5 to about 10.5.

Finally, of course, the invention can be used in an assay to detect an oxidase in biological samples. For example, such an assay involves:
(a) providing a solid support, such as a tube, coated with an antibody to oxidase;
(b) incubating the sample containing the oxidase to be assayed in the presence of the solid support prepared in stage (a);
(c) washing the support;
(d) adding to the support prepared in stage (c) a substrate associated with the oxidase, an enhancer, and a chemiluminescent reagent maintained at a pH of about 9.5 to about 10.5; and
(e) measuring the chemiluminescent response and deducing the concentration of the oxidase from the measurement thereby performed.

A kit of reagents for carrying out this method, which also forms the subject of the present invention comprises:
(a) a solid support, such as a tube, coated with an antibody possessing specificity for an oxidase; and
(b) a substrate associated with the oxidase, a chemiluminescent reagent, and an enhancer, maintained at pH from about 9.5 to about 10.5.

As a chemiluminescent reagent, luminol, isoluminol, N-(4-aminobutyl)-N-ethyl isoluminol, or lucigenin can be chosen; preferably, luminol is chosen.

In examples which follow, the advantages and applications of the present oxidase enzyme system in immunoanalysis is illustrated o the basis of actual experimental results.

EXAMPLE 1

Assay of Xanthine Oxidase in Liquid Phase

An example of an optimized procedure for assaying xanthine oxidase (XO) activity in liquid phase is described below.

a) Procedure

The sample xanthine oxidase to be analyzed (50 $\mu$l) was diluted in 0.1M sodium barbital solution containing bovine albumin (0.2%) and ethylenedia-minetetraacetic acid, disodium salt (EDTA) (1 mM), and mixed with 50 $\mu$l of a solution of hypoxanthine (10 mM) substrate and luminol ($0.5 \times 10^{-4}$M) in distilled water.

The light measurement was then performed in front of the photomultiplier of a luminometer (PICOLITE 6500 ™ Packard Instruments Co.). The emission of photons was measured for a period of one second at room temperature. The results obtained are expressed as counts/second after subtracting the background (counts/second corresponding to the emission of light by the medium in the absence of xanthine oxidase).

This procedure was characterized by the extreme ease and extreme rapidity with which it was carried out, as well as by the possibility of automating the counting therein.

b) Kinetics of the Reaction

The main value of this reaction resides in the great stability and duration of the chemiluminescent signal obtained.

Figure 1:
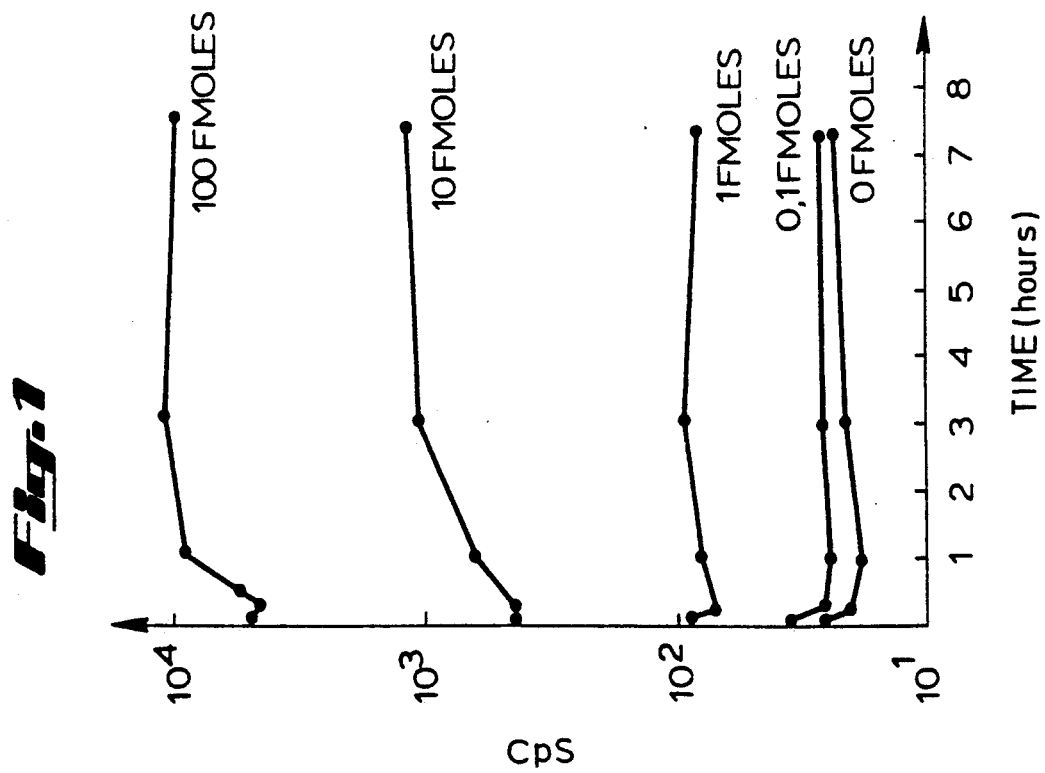

The kinetics of the xanthine oxidase-dependent oxidation of luminol for different enzyme samples are shown in FIG. 1. The experimental conditions are those described above. The measurements for a period of one second, at intervals over a period of eight hours, demonstrate the stability of the signal. It should be noted that, for xanthine oxidase samples less than l femtomole (fmol), complete stabilization of the emission is attained 10 minutes after the start of the reaction. On the other hand, for higher concentrations in the range 10 to 100 fmol per sample, the signal gradually increases and stabilization is obtained in one hour. In point of fact, these variations of light output remain negligible with respect to the measurement time.

Comparing the kinetics of this chemiluminescent response with that corresponding to the other stable systems which have been described at the present time demonstrate the value of xanthine oxidase in immunoanalysis: The measurements can be repeated without loss of sensitivity for a very extended period of time.

Other results have shown that the signal can be measured for periods of at least 20 hours.

The stability of the emission of photons can be interpreted in accordance with the catalytic nature of the xanthine oxidase reaction, the stability being linked to the gradual accumulation of $H_2O_2$ originating from the dismutation of $O_2^-$. This sequence then brings into play the HABER-WEISS reaction which is responsible for the formation of hydroxyl radicals and the subsequent oxidation of luminol generating light. Henry J. P., Michelson A.M. (1977) in Superoxide and Superoxide Dismutases—Ed. by Michelson A.M., McCord J. and Fridovich I. pp. 283-290, Academic Press.

GENERAL CHARACTERISTICS OF THE CHEMILUMINESCENT REACTION

Apart from the stability of the signal, the general characteristics of the XO reaction are as follows:

a) Influence of the Molarity of the Medium

Chemiluminescent response obtained for variable concentrations of barbital between 0.025M and 0.25M demonstrated that the stronger the molarity, the greater the responses. A final barbital concentration of 0.25M was consequently adopted for the routine procedure.

b) Influence of the pH of the Medium

The chemiluminescent responses of the XO system was optimized with the use of alkaline range buffers. Use of buffers with pH ranging from about 9.5 to about 10.5 yielded increases in light production of 10-100 times compared to lower pH's. Useful buffers include phosphate, borate, carbonate, barbital and TRIS.

c) Influence of the Nature of the Chemiluminescent Compound

Luminol does not represent the only substance whose oxidation leads to the emission of photons in the XO system. This property is also shared by lucigenin (N-methyl acridinium).

An experiment determined the respective concentrations of lucigenin ($10^{-5}$M) and luminol ($0.5 \times 10^{314}$M) giving the greatest chemiluminescent response for an XO sample of 23 ng (77 femtomoles).

The use of luminol provided much greater sensitivity (<0.3 femtomoles) than that obtained with lucigenin. This fact is probably linked to the special reactivity of luminol with respect to oxygen-containing radicals produced by the XO reaction ($O_2^{\cdot-}, H_2O_2, OH^\circ$), whereas lucigenin is more specific for the superoxide anion. In this case, the information contributed by the hydrogen peroxide and the hydroxyl radicals is not taken into account. The use of luminol at a final concentration of $0.5 \times 10^{-4}$M) was hence adopted for the routine xanthine oxidase assay procedure.

d) Influence of the Nature of the Substrate

FIG. 2 shows the comparison of the curves for light emission in terms of time during the xanthine oxidase-dependent oxidation of luminol, with two different substrates, hypoxanthine and acetaldehyde, and with two different concentrations of xanthine oxidase.

Legend of FIG. 2

| | |
|---|---|
| -------- | 5 mM hypoxanthine |
| ———— | 50 mM acetaldehyde |
| X———X | 80 femtomoles XO |
| •———• | 0.8 femtomole XO |

The stability of the signal obtained with hypoxanthine was much more pronounced than that which corresponds to acetaldehyde. In this latter case, in effect, the decrease occurs after an interval of 20 minutes following the initiation of the reaction. After 150 minutes, the intensity of the signal with acetaldehyde represents only 4% of the maximal response achieved with hypoxanthine. In the case of hypoxanthine, no decrease was observed at this point in time. This justifies the routine use of hypoxanthine as a substrate for obtaining an emission of photons which is both stable and high.

e) Potentiation of the XO-Dependent Oxidation of Luminol by the Iron/EDTA Complex It is generally accepted WINTERBOURN C.C. et al, *Archives of Biochemistry and Biophysics*, 244, 1, 27–34, 1986) that the iron/ethylenediaminetetra acetic acid (EDTA) complex represents an efficient catalyst for the HABER-WEISS reaction according to the following mechanism:

$$Fe^{3+}(EDTA) + O_2^{\cdot-} \rightarrow Fe^{2+}(EDTA) + O_2$$

$$Fe^{2+}(EDTA) + H_2O_2 \rightarrow Fe^{3+}(EDTA) + OH^- + OH^\circ$$

Figure 3:
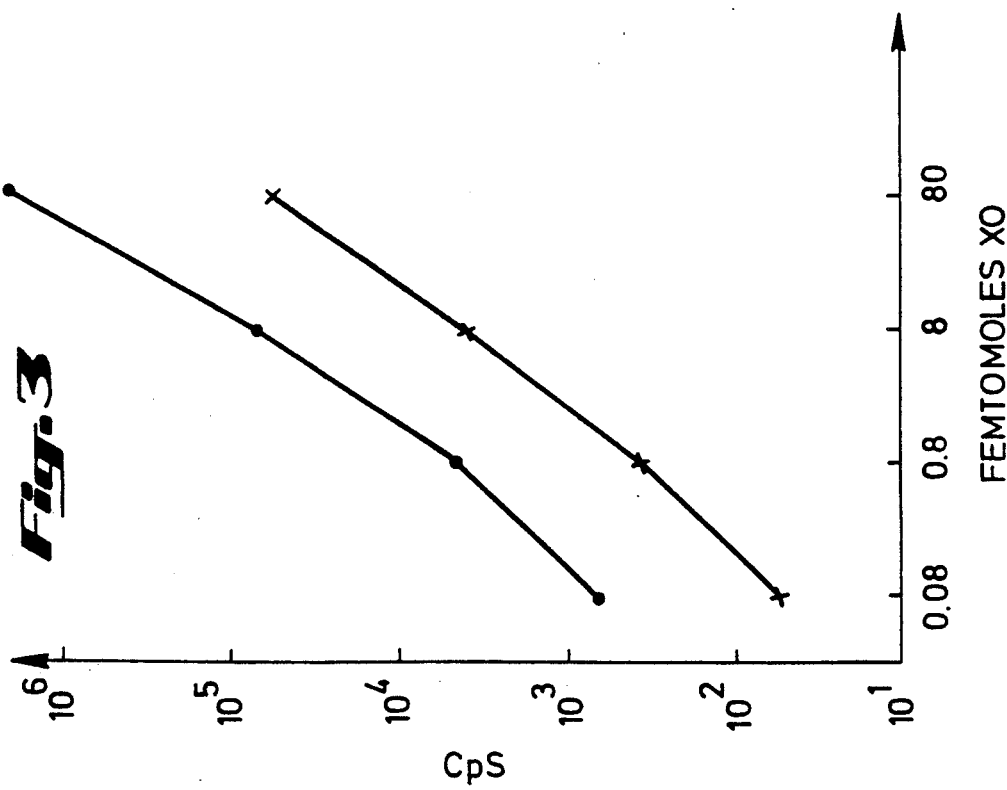

FIG. 3 shows the chemiluminescence curves measured 15 minutes after triggering the reaction with XO and obtained in the presence or absence of iron/EDTA complex.

Legend of FIG. 3

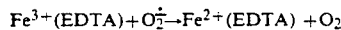
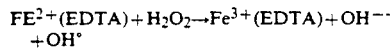

•———• 5 μM EDTA-Fe
x———x 0 μM EDTA-Fe

The iron complex was prepared by mixing equal parts of $FeCl_2$ (1 mM) and EDTA-$Na_2$ (100 mM) solution, both prepared in distilled water. After a minimum time of 30 minutes elapsed, this solution was diluted 1/100 in the hypoxanthine/luminol mixture. The final concentration of the complex in the incubation medium for the XO reaction is hence 5 μM.

The EDTA/iron complex increases by a factor of 10 the chemiluminescent response linked to the XO-induced oxidation of luminol. The use of the complex hence enables the threshold of detection of the XO activity to be lowered.

Figure 4:
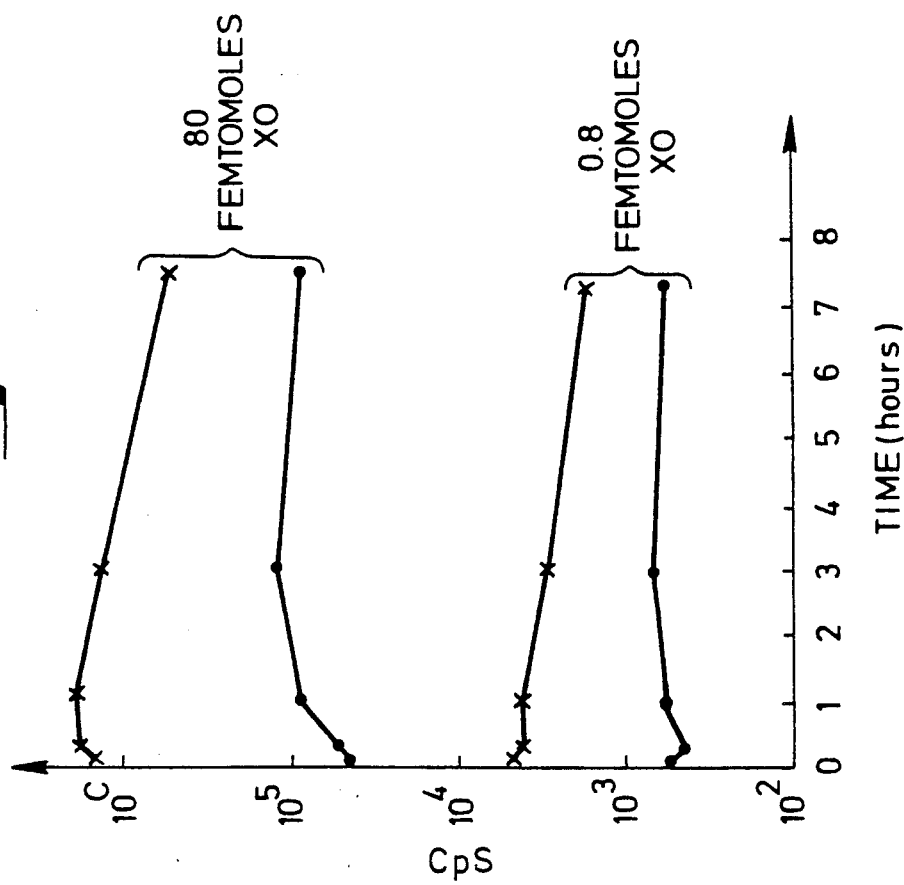

FIG. 4 shows, furthermore, that the signal produced in the presence of this complex was slightly less stable than that obtained in its absence; however, 7 hours 30 minutes after initiation of the reaction, the emission of photons obtained and measured as chemiluminescence in the presence of Fe/EDTA remained much higher than that observed in its absence.

Legend of FIG. 4

Kinetics of the xanthine oxidase-dependent oxidation of luminol in the presence X—X or absence .—. of EDTA/Fe complex (5 μM), for concentrations of xanthine oxidase of 0.8 and 80 femtomoles.

These properties show that the iron/EDTA complex represents a good amplification agent for the reaction in question and that its use is recommended in the routine assay procedure.

EXAMPLE 2

Solid Phase Assay of Avidin

1. Preparation of the XO-Biotin Conjugate

A suspension of XO in 3.2M $(NH_4)_2SO_4$ (20 mg/ml) (Boehringer Mannheim) was centrifuged at 5000g during 10 minutes and the pellet was dissolved in 1 ml pH 8.5 50 mM, NaCl, 20 mM borate buffer. A solution of biotin X NHS (Biotin ε-aminocaproic acid N hydroxysuccinimide ester, Calbiochem) (1.2 mg/12 12 μl anhydrous dimethylformamide) was added. The solution was agitated by vortexing for two minutes, left at ambient temperature for one hour, and then dialyzed against 0.13M NaCl, 0.07M Na phosphate buffer pH 7.4 (Phosphate buffered saline PBS) containing 0.1% Na azide. The XO-biotin conjugate was then kept at +4° C. under sterile conditions.

2. Bovine Serum Albumin Biotin Conjugate 50 mg bovine serum albumin (BSA) (Fraction V, Fluka) were dissolved in pH 8.5 50 mM NaCl, 20 mM borate buffer. A solution of biotin X NHS (20 mg/200 μl anhydrous dimethylformamide) was then added, and the following steps were identical to those described for the preparation of biotinylated XO.

3. BSA-Biotin Coated Tubes

150 μl of biotinylated BSA (5 μg/ml) in pH 9.6 0.1M carbonate buffer were added to polystyrene tubes (SARSTEDT, 3.5ml, 55×12 mm). The tubes were incubated at +4° C. for 16 hours, then washed twice with distilled water and the remaining protein binding sites of the tube were saturated with a 0.3% solution of BSA (500 μl) in distilled water containing 0.1% sodium azide.

4. Avidin Assay

BSA biotin coated tubes were washed twice with 1 ml of phosphate buffered saline (PBS) containing 0.1% BSA, then 200 μl of a solution containing various concentrations of egg avidin (Calbiochem) were added. The tubes were incubated 30 minutes at ambient temperature.

Figure 5:
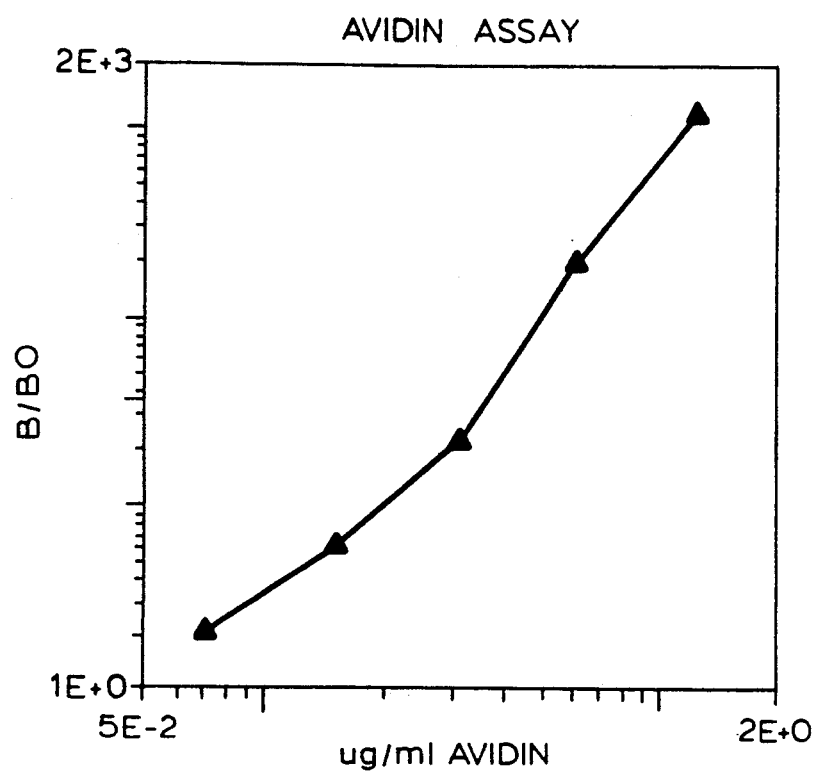

After washing the tubes twice with PBS containing 0.1% BSA (PBS BSA), the XO biotin (2 μg/200 ml PBS BSA) was added and the tubes were again incubated two hours at ambient temperature. The tubes were washed, then the signal reagent (200 μl) was added. The composition of the signal reagent was the following:

$0.5 \times 10^{-4}$ M luminol
0.25M Na barbital buffer pH 10.2
5 mM hypoxanthine
0.25 mM $Na_2$ EDTA
5 μM $Fe^{2+}Cl_2$ The tubes were placed in the luminometer and the counting was performed for five seconds. FIG. 5 shows a representative example of an avidin assay performed with this protocol.

Legend of FIG. 5

Abscissa: Concentration of avidin in μg/ml (log scale).
Ordinate: Ratio of counts per second in presence and in absence of avidin (log scale).

It was thus demonstrated that the magnitude of the light intensity produced by the XO dependent chemiluminescent system was a function of the quantity of avidin present in the specific binding reaction mixture. The present invention thus provides conjugates (biotinylated - XO) useful for the determination of ligands in a liquid medium by a solid phase assay.

EXAMPLE 3

Solid Phase Competitive Biotin Assay

The steps of the biotin competitive binding assay were as follows:

A preformed complex biotinylated XO (10 μg/ml) Streptavidin (0.3 μg/ml) was prepared in PBS BSA, and incubated 30 minutes at ambient temperature. This was added to BSA-biotin coated tubes, prepared as previously described: 100 μl of a solution containing various concentrations of biotin, and 100 μl of the preformed complex. Afterward, the tubes were incubated for two hours at ambient temperature (or overnight at +4° C). Then the tubes were washed twice with 1 ml of PBS BSA. The chemiluminescent signal reagent (200 μl) was then added and the tubes counted in the luminometer during five seconds.

Figure 6:
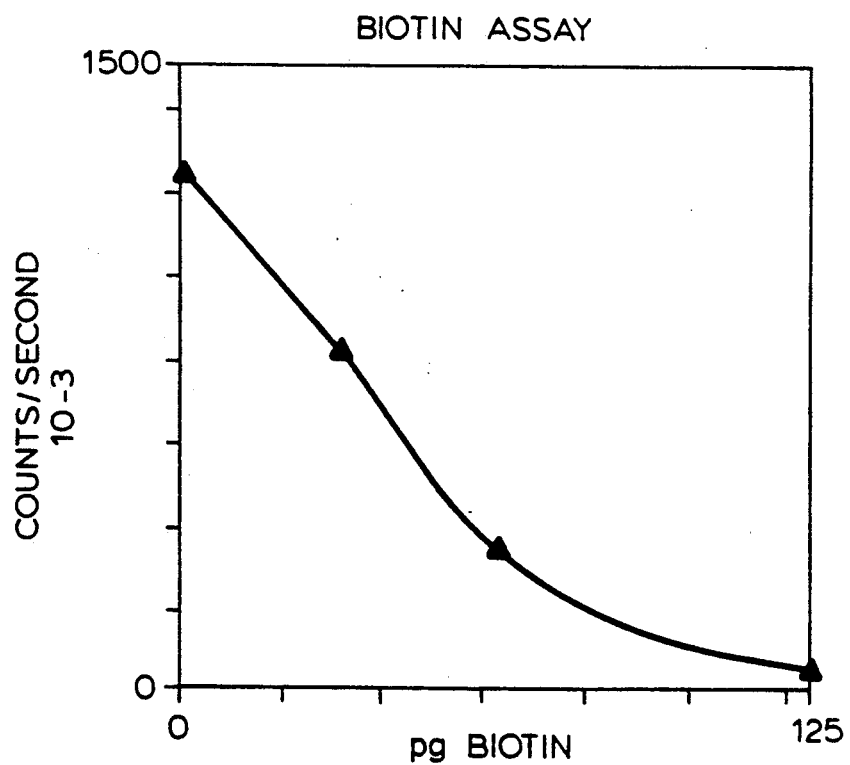

FIG. 6 shows a representative example of a competitive assay performed with this protocol. The sensitivity of this assay is about 5 pg (20 femtomoles).

Legend of FIG. 6

Abscissa: Concentration of biotin in pg per sample (linear scale).
Ordinate: Counts per second (linear scale).

The magnitude of the light intensity produced by the XO dependent chemiluminescent system was an inverse function of the quantity of biotin in the specific reaction mixture. The present invention thus provides complexes useful as tracer for the determination of ligands in a liquid medium by a competitive solid phase assay.

EXAMPLE 4

Detection of Toxoplasma Antibodies a) Preparation of Biotinylated Antihuman IgG 0.7 ml of a 2.8 mg/ml rabbit antibody to human IgG solution in 0.25M NaCl, 0.02M phosphate pH 7.6 buffer (Jackson Laboratories) was added to 8 μl of a solution of Biotin X NHS (10 mg/100 μl dimethylformamide). The following protocol was then identical to that described for the biotinylation of XO.

b) Toxoplasma Antigen Coated Tubes

The Toxoplasma antigen preparation had been purchased from Institute Virion (Zurich, Switzerland) and reconstituted according to the recommended instructions provided. Polystyrene tubes were coated with 150 μl of reconstituted antigen preparation, and incubated overnight at ambient temperature. They were kept dry at −20° C. after washing with PBS BSA buffer.

c) Preformed Biotinylated XO—Streptavidin—Biotinylated Anti IgG Complex

A complex biotinylated XO—streptavidin—biotinylated rabbit IgG was prepared in PBS BSA by incubating biotinylated XO (10 μg/ml) with streptavidin (0.5 μg/ml) for 15 minutes at ambient temperature, then adding biotinylated rabbit IgG (final concentrations: 1.4 μg/ml).

d) AntiToxoplasma Assay

The steps of the Toxoplasma antibody assay were as follows:

Coated tubes were incubated with 200 μl of positive or negative control serum for one hour at −37° C. The Toxoplasma control sera were purchased from Biotrol Laboratories. The tubes were then washed with PBS BSA buffer and preformed complex (200 μl) added. The tubes were incubated three hours at ambient temperature (or overnight at 4° C.), and then washed twice with PBS BSA. Afterward, 200 μl of the chemiluminescent signal reagent was added as described above and the tubes counted in luminometer for five seconds.

Figure 7:
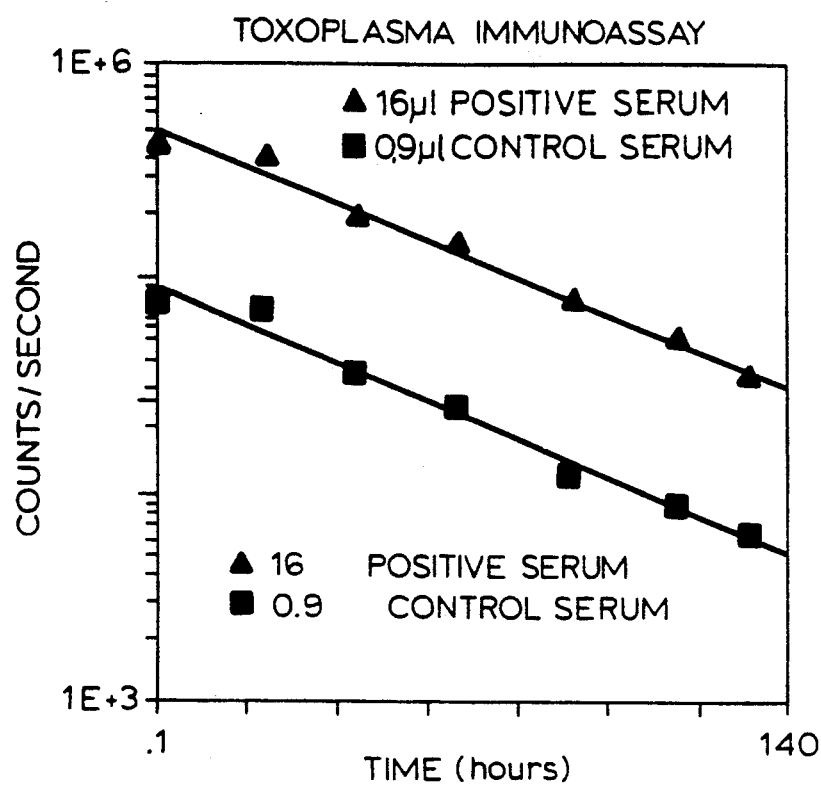

An example of the kinetics of the chemiluminescent signal, obtained with two different dilutions of a Toxoplasma positive control serum, is shown in FIG. 7. The maximal signal appeared within 30 minutes following the addition of the signal reagent, the signal decreases with a half life of 30 hours.

Legend of FIG. 7

Abscissa: Time (hours) (linear scale)
Ordinate: Counts/second (logarithmic scale)

Figure 8:
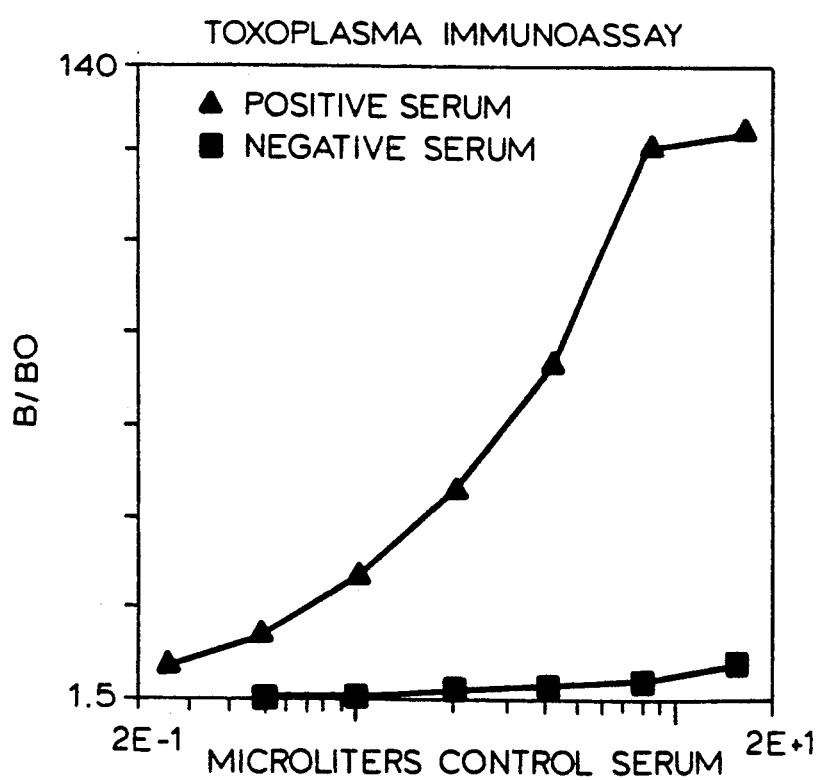

FIG. 8 shows the chemiluminescent responses obtained with serial dilutions of both positive and negative control sera.

Legend of FIG. 8

Abscissa: Microliters, control serum (logarithmic scale)
Ordinate: Ratio of counts per second in presence and in absence of diluted sera (logarithmic scale)

The intensity of a chemiluminescent signal produced by a complex [biotinylated XO—Streptavidin—biotinylated anti-human IgG antibody] which is immobilized on a solid phase, itself coated with the corresponding antigen, was directly related to the quantity of human IgG to Toxoplasma in the sample to be analyzed. Further, the obtained signal presented a long time emission, on the order of days.

Similar results were obtained for an assay designed in the same manner as the Toxoplasma antibody assay, and allowing the detection of Chlamydiae antibody in human serum.

EXAMPLE 5

Prolactin Immunoassay

Two monoclonal antibodies directed at separate epitopes of the prolactin molecule used in this immunoassay were a generous gift of Immunotech (Luminy, France).

a) Preparation of Biotinylated Monoclonal Antiprolactin Antibody 1 mg of IgG$_1$ monoclonal antiprolactin antibody in 0.75 ml of 0.15 mM NaCl, 20 mM borate, pH 8.6 buffer was treated with 40 µg of biotin X NHS dissolved in 20 µl of dimethylformamide. The remaining protocol was then identical to that described above for the preparation of biotinylated XO.

b) Antiprolactin Antibody Coated Tubes

Polystyrene tubes were coated with 19.5 µg of an IgG$_2$ monoclonal antibody in 150 µl 0.1M carbonate buffer, pH 9.6. The coating was performed overnight at ambient temperature, then the tubes were washed once with distilled water, and the residual protein binding sites were saturated with 500 µl of a 0.3% BSA solution in distilled water. The coated tubes were kept at +4° C.

c) Prolactin Immunoassay

The steps of the prolactin immunoassay were performed as follows:

Incubating the coated tubes with 150 µl of antiprolactin biotinylated antibody diluted in PBS BSA (10$^{-2}$ dilution) and 50 µl of serum overnight at ambient temperature.

Washing the tubes twice with PBS BSA.

Adding 200 µl of the preformed complex: Biotinylated XO (10 µg/ml), Streptavidin (0.5 µg/ml) prepared in PBS BSA and incubating two hours at ambient temperature.

Washing the tubes twice with PBS BSA.

Adding 200 µl signal reagent.

Counting each tube in the luminometer for five seconds.

The half life of the chemiluminescent signal corresponding to the concentration of 200 µg/ml was 30 hours. The comparison of the standard curves obtained 30 minutes, 21 hours, and 140 hours after the addition of signal reagent showed that the standard curves resulting from determining the chemiluminescence over this time course were essentially equivalent. The sensitivity appeared to improve with time because of the proportionately more rapid decay of the background. (FIG. 9)

Figure 9:
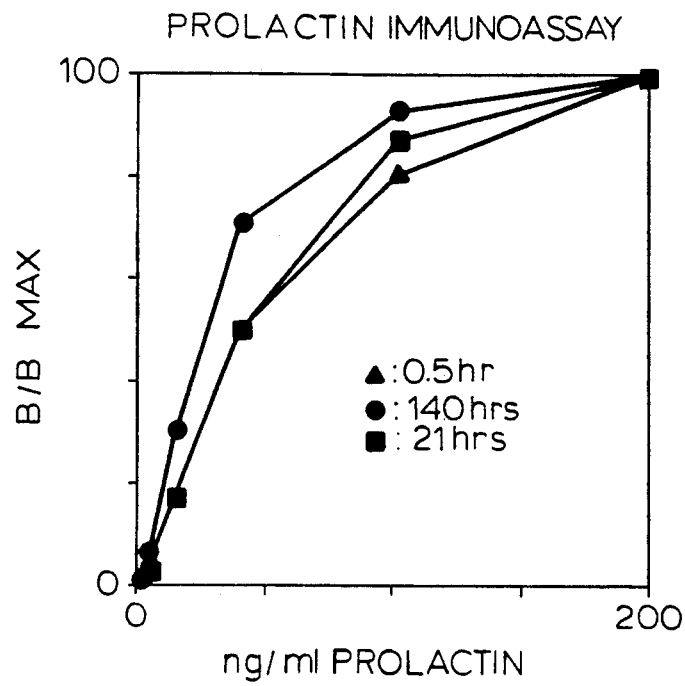

Legend of FIG. 9

Abscissa: ng/ml prolactin (linear scale)

Ordinate: Ratio of counts per second obtained with the different standard sera to that obtained with the maximal concentration (200 ng/ml) (linear scale)

This thus demonstrated that the magnitude of the chemiluminescent signal produced by a complex [biotinylated XO—Streptavidin—biotinyl monoclonal antibody], immobilized by the way of the antigen on a solid phase, which is itself coated with a complementary monoclonal antibody, is directly related to the quantity of antigen in the sample. Also, the obtained signal demonstrated a long-lived emission, which can be expressed in terms of days.

EXAMPLE 6

Triiodothyronine Immunoassay a) Preparation of the Tracer 1.19 mg of biotinylated BSA was diluted in pH 9.6, 0.1M carbonate buffer (3ml). 12 ml of 0.04M barbital buffer pH 9.4 are added, then 2.5 mg of triiodothyronine (T$_3$), previously dissolved in 1 ml dimethylformamide. The coupling reaction was initiated by adding 50 µl of 0.04M glutaraldehyde in distilled water. The mixture was incubated for three hours at ambient temperature, then the reaction was stopped by the addition of 200 µl 0.1M glycine in distilled water. After an additional hour incubation, 100 µl of a 37.5 mM sodium borohydride solution were added. The mixture was kept at 4° C. for 1.5 hours. The solution was filtration-concentrated to 1.5 ml (Amicon B15) and then the conjugate purified by gel filtration column chromatography (Ultrogel AcA 44, Industrie Biologique Francaise) (Size of the column: 60×0.9cm). The immunoreactive and enzymatically active fractions were respectively located by radioimmunoassay and by chemiluminescence in the hypoxanthine, luminol system. These fractions were pooled.

b) Coated Tubes

Polystyrene tubes were coated with 150 µl 1.95 µg/150 µl of a goat antirabbbit IgG (ARGG) (Jackson Laboratories) in 0.1M carbonate buffer pH 9.6. The incubation was performed overnight at ambient temperature, then the tubes were washed and the unreacted protein binding sites were saturated with 500 µl of a 0.3% BSA solution in distilled water. These coated tubes were kept at +4° C.

c) Anti T$_3$ Antibody

Anti T$_3$ antibody was obtained by immunizing a rabbit with a T$_3$ BSA conjugate derivatized with carbodiimide. The immuno-globulin was purified with 30% (NH$_4$)$_2$SO$_4$ precipitation, and then by DEAE Sephacel (Pharmacia, Uppsala, Sweden) chromatography.

d) T$_3$ Immunoassay

The steps of the T$_3$ assay were as follows:

Incubating (3 hours, ambient temperature) ARGG coated tubes with various concentrations of T$_3$ (0 to 12.4 p moles), a fixed concentration of T$_3$ biotinylated BSA conjugate, and anti T$_3$ antibody (final dilution: 1/15000). All dilutions are performed in PBS BSA. The final volume of incubation is 300 µl Washing the tubes with PBS BSA, containing 0.05% TRITON X100

Incubating (2 hours, ambient temperature) the tubes with the preformed complex biotinylated XO (10 µg/ml),—Streptavidin (0.5 µg/ml).

Washing the tubes with PBS BSA.

Adding 200 µl of the signal reagent.

Counting each tube in the luminometer for 5 seconds.

Table I shows the results obtained with two different dilutions (10$^{-3}$, 10$^{-4}$) of the T$_3$ biotinylated BSA conjugate. CPS means counts per second; B/Bo means CPS bound at concentration B divided by CPS bound in absence of T$_3$.

| T$_3$ pmoles | T$_3$ Biotinylated BSA | | | |
|---|---|---|---|---|
| | 10$^{-3}$ | | 10$^{-4}$ | |
| | CPS | B/Bo | CPS | B/Bo |
| 0 | 70810 | 1.0 | 51500 | 1.0 |
| 0.124 | 48010 | 0.68 | 6530 | 0.13 |
| 1.24 | 11100 | 0.16 | 1080 | 0.02 |
| 12.4 | 1020 | 0.01 | 850 | 0.01 |

The intensity of the chemiluminescent signal produced by a complex [biotinylated XO—Streptavidin—hapten—biotinylated BSA], immunologically immobilized on a solid place was inversely related to the quantity of hapten in the sample.

EXAMPLE 7

Triiodothyronine Immunoassay Using T$_3$-XO Conjugate

An example of application of the chemiluminescent system in immunoanalysis using hapten XO conjugate is provided by the competitive immunoassay of triiodothyronine.

a) Preparation of the T₃-XO Conjugate

The coupling of T₃ (Fluka) with a preparation of XO (BOEHRINGER) was performed according to the method of YAMAMOTO, *Clinical Chemistry.* 27-10, pages 1721-1723, 1981.

XO was equilibrated in 0.1M phosphate buffer, pH 7, by passage through a Sephadex G-25 column (Pharmacia PD-10) in two successive chromatographic runs. The ratio of the absorbancies at 280 nm and 450 nm of the preparation obtained equaled $5.8 +/- 0.2$.

600 μl of a solution of T₃ containing 1 mg/ml in dimethylformamide (DMF) was treated with 60 μl of a solution of 4-(maleimidomethyl) cyclohexane-1 carboxylic acid succinimide ester (SMCC) in DMF (2 mg/ml), and 1.2 ml of phosphate buffer were then added. The mixture was incubated at 30° C. for 90 minutes with vigorous agitation on a vortex mixer every five minutes.

The activation reaction was stopped by adding 0.1M glycine (120 μl). The actual T₃-XO coupling was performed by mixing 100 μg of XO equilibrated in phosphate buffer (200 μg) with 150 μl of the activated T₃ solution from above. Incubation was performed for 30 minutes at 30° C., and the reaction was then stopped by adding 0.1M mercaptoethylamine in phosphate buffer.

The reaction medium was then purified on an Ultrogel AcA (Industrie Biologique Francaise) column with 0.1M phosphate buffer, pH 7, containing 0.2% bovine serum albumin (BSA) as eluant. The XO enzyme activities were measured for each fraction. The fractions containing the coupling derivative, T₃-XO, were localized after binding the latter to tubes coated with anti-T₃ antibodies prepared using IgG obtained in rabbits. After addition to each coated tube of 100 μl of fraction diluted in 0.1M barbital buffer, pH 8.6, containing 0.1% of BSA, incubation was performed for one hour at 37°. The tubes were washed with distilled water and the immobilized XO activities determined by adding 200 μl of signal reagent.

Figure 10:
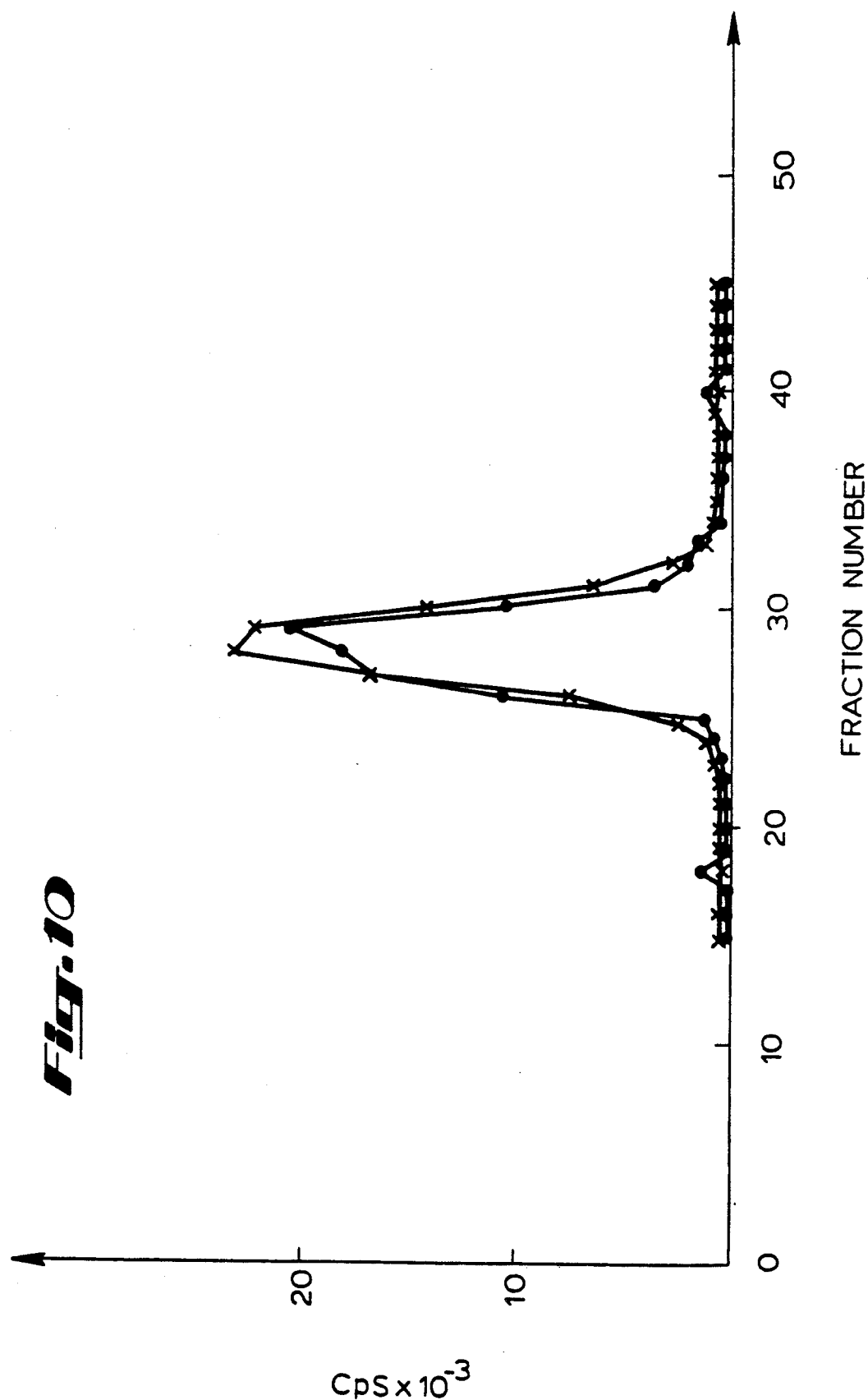

FIG. 10 shows the results of the binding to the anti-T₃ solid phase after the passage of the coupling medium through an Ultrogel AcA 34 column. An immunoreactive peak was localized and the corresponding fractions were combined.

Legend of FIG. 10

X____X  total XO activity

●____●  XO activity bound to the Anti-T₃ solid phase b) Immunoassay of T₃ by a Competitive Binding Procedure

Figure 11:
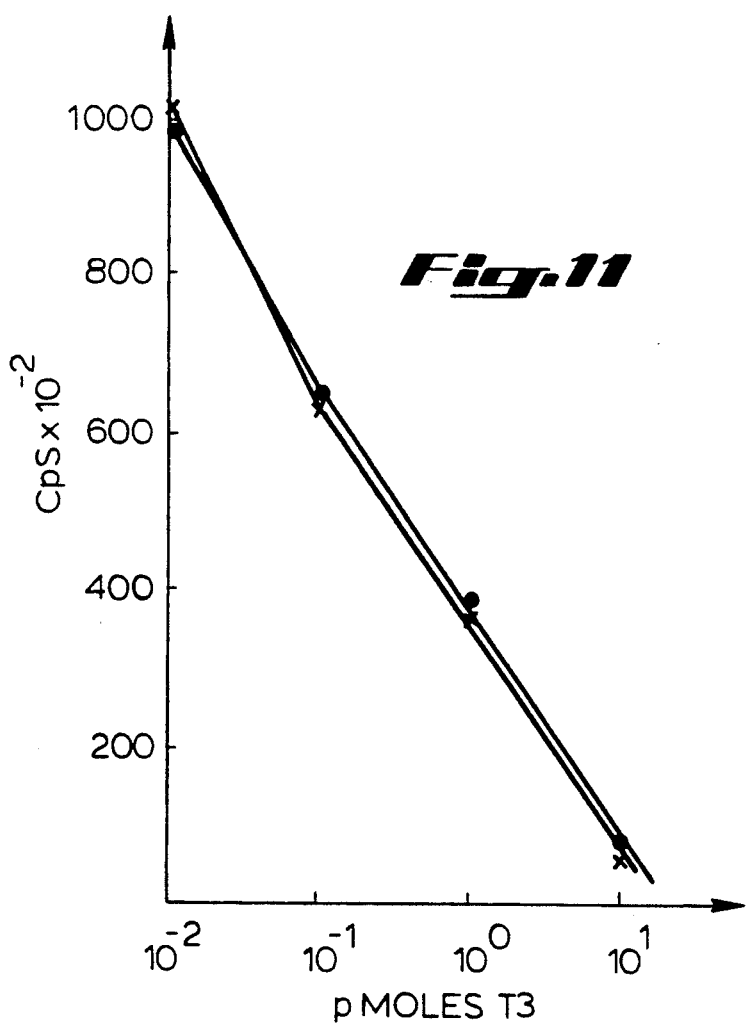

The tracer obtained above was used to carry out an immunoassay of T₃. FIG. 11 shows the corresponding calibration curve.

Legend of FIG. 11 o____o  counting for 1 second performed 15 minutes after the start of the reaction x____x  counting for 1 second performed 16 hours after the start of the reaction Abscissa: pmol of T₃ (logarithmic scale)
Ordinate: counts per second $\times 10^{-2}$ (linear scale)

The assay employed tubes coated with anti-T₃ IgG described above. The incubation medium consisted of variable concentrations of T₃ between 10 and 0.1 pmol in a volume of 100 μl in the presence of the tracer (100 μl).

All the dilutions were performed in 0.iM barbital buffer, pH 8.6, containing 0.1% of BSA. The incubation period at 37° was one hour. The determination of the immobilized XO activity was performed as described above.

The amount of light generated by the XO-mediated chemiluminescent reaction after 16 hours of reaction demonstrated only a small decrease in the light output when compared to the light output measured after 15 minutes of reaction. Stability of the XO-dependent chemiluminescent reaction, both in the solid phase and in the liquid phase, may hence be inferred.

EXAMPLE 8

Detection of a Biotinylated Lambda DNA Immobilized on a Solid Support

Lambda phage DNA was biotinylated by nick translation using commercially available reagents (ENZO BIOCHEMICALS, N.Y., U.S.A.). The obtained preparation containing 1% biotin (w/w) was spotted on a nylon membrane (0 ng/2 μl, 2 ng/2 μl, 20 ng/2 μl, 200 ng/2 μl), denaturated, in situ neutralized, and then irreversibly immobilized by ultraviolet irradiation (254 nm). The detection of this immobilized biotinylated DNA was performed as follows:

The membranes were saturated with PBS containing 3% BSA for at least one hour at ambient temperature;

A solution of the preformed complex biotinylated XO (5 μg/ml) - Streptavidin (0.5 μg/ml) in PBS containing 3% BSA was transferred to the membranes and incubated for two hours at ambient temperature;

The membranes were washed twice in PBS, containing 3% BSA and 0.05% TRITON X 100 (v/v) for 10 minutes at ambient temperature;

The spots corresponding to the various doses of biotinylated lambda DNA were cut and placed in signal reagent (0.5 ml);

The tubes were counted in the luminometer for five seconds.

The following results were obtained:

| Biotinylated DNA (ng/2 μl) | Counts Per Second |
| --- | --- |
| 0 | 6100 |
| 2 | 22436 |
| 20 | 53480 |
| 200 | 81445 |

It was thus demonstrated that the XO dependent luminescent response is related to the amount of biotinylated lambda DNA, immobilized on a solid support.

EXAMPLE 9

Detection of Human Papilloma Virus Infection (HPV) by Dot Hybridization

Human papilloma virus was detected by dot hybridization using biotinylated probes and an XO-Streptavidin (XO-SA) conjugate.

a) Preparation of XO-SA Conjugate

The conjugate XO-SA was prepared by using the heterobi-functional reagent sulfosuccinimidyl 4 (N-maleimido methyl) cyclohexane -1- carboxylate (sulfo SMCC, Pierce). Briefly, 10 mg of XO, equilibrated in I ml of ph 7.3, 0.1 M phosphate buffer containing, 1 mM EDTA, is thiolated by reacting with iminothiolane (Sigma, molar ratio iminothiolane/XO =100) during 4 h at ambient temperature under nitrogen. The reaction mixture is then subjected to gel filtration on a PD-10 columm (Pharmacia Fine Chemicals) using degassed coupling buffer as eluent.

During the XO activation time, 4 mg of streptavidin (Sigma) equilibrated in the degassed coupling buffer, is reacted with sulfo SMCC (molar ratio sulfo SMCC/SA =20) for 10 minutes at ambient temperature under nitrogen. The reaction is stopped by addition of 10 μl of 0.5M glycine, and the mixture is subjected to gel filtration on a PD10 column using degassed coupling buffer as eluent.

The coupling reaction is then performed by mixing thiolated XO with maleimide-SA (molar ratio SA/XO: 2) and incubating for 15 h at +4° C. The reaction mixture is purified by Sephacryl S 300 chromatography (Pharmacia Fine Chemicals; size of the column: 0.9×60 cm) with pH 6.5, phosphate 0.1M buffer containing sodium salicylate (1 mM), $Na_2$ EDTA (1 mM), bovine serum albumin (0.1%) and sodium azide (0 !%). For each fraction, the XO dependent chemiluminescent activity and the fixation of the conjugate onto a biotin-albumin solid phase are determined. The active fractions are then selected and pooled.

b) Preparation of Biotinylated Probes

The specific biotinylated type 16 HPV DNA probes were obtained by random priming (Boehringer kit). Biotinylated DNA is recovered by gel filtration on a Sephadex G 50 column equilibrated with SDS (0.1%).

c) Hybridization

The target consists of genomic DNA in which are integrated 1 to 500 copies of HPV gene. The hybridization is performed with DNA probes consisting of more than 200-bp. 1 to 5 ml of denatured samples, diluted in 10×SCC (1×SCC buffer : 0.15M NaCl, 15 mM Na 3 citrate), are spotted on nitrocellulose filters (Schleicher and Schuell BA 83). The filters are dried at ambient temperature, then fixed at 100° C. for one hour and kept dried.

The filters are then prehybridized for two hours at 50° C. in hybridization buffer 2×SCC, 5×FP Ge, 2 mM EDTA, salmon sperm DNA 0.2 mg/ml (FP Ge solution : 0.02% gelatin, polyvinylpyrolidone, Ficoll). The hybridization is performed for two hours at 50° C. in the same buffer with the biotinylated probe (10 ng/ml).

d) Detection

The filters are then washed 3×10 min at 37° C. with 0.2 ×SCC containing 0.2% Tween 80, and saturated for one hour in pH 7.5 100 mM Tris buffer containing 150 mM Na Cl, 3% gelatin, 0.2% Tween 80. The filters are incubated in the same buffer with the XO-SA conjugate (1 μg/ml) for 10 minutes, and then washed 3×10 min with pH 7.5 100 mM Tris buffer containing 150 mM, NaCl, 0.2% Tween 80 and with 2×SCC.

e) Luminescence Measurement

After the washing steps, the filters are dried, then incubated in a polythylene bag with 1 ml of signal reagent (0.2M borate buffer pH 10.2, containing 1 mM hypoxanthine, 25 μM luminol, 20 μM Na perborate, 62.5 μM Fe EDTA complex; EDTA/Fe molar ratio : 20). The light emission is detected using a photon counting camera system (Argus 100, Hamamatsu) consisting of a video camera, a luminescence amplifier, and an imaging analyzer system. The number of photons emitted in each area of interest are determined after a five minute exposure time.

f) Results

As depicted in Table II, the obtained detection threshold is about 1 pg of homologous target.

TABLE II

| pg homologous target | 0 | 1 | 10 | 100 |
|---|---|---|---|---|
| photons/5 min | 5 000 | 7 500 | 45 000 | 350 000 |
| ±2 SD | ±800 | ±1 200 | ±5 000 | ±2 800 |

The xanthine oxidase label can be used for the detection of a single gene. It is thus possible to detect one copy of an integrated papilloma virus gene per genome by performing a hybridization with 10 μg of human DNA. The obtained signal is three-fold that of the background if a large size probe (2000-bp) is used.

EXAMPLE 10

Detection of Base Mutations in Human DNA a) Preparation of XO-SA Conjugate

See EXAMPLE 9.

b) Labeling of Oligonucleotides

The probes are obtained from 5'end amino desoxynucleotides corresponding to a highly polymorphic region of the HLA system (DQβ1). The biotinylation is performed by reacting biotin N hydroxsuccinimide (1.0 mg/100 μl of dimethyl formamide) with the 5' end amino oligonucleotide (100 μg/100 μl of pH 9.5, 0.2M carbonate buffer).

c) DNA Amplification

DNA amplification was performed by polymerase chain reaction (PCR) as described by KOGAN S.C., DOHERTY M., GITSCHIIER J., *N. England J. Med.* 16:985-990 (1987). Two primers, defining a 240 bases of DQβ1 region, are used. Briefly, the PCR is performed in a 100 μl reaction medium containing 1 μg of genomic DNA, 0.2 mM d ATP, d CTP, d GTP, d TTP, 1 mM of each primer in 1 × reaction buffer (16.6 mM $(NH4)_2$, SO4, 67 mM Tris HCl pH 8.8, 6.7 mM Mg $Cl_2$, 10 mM β mercaptoethanol, 6.7 mM EDTA, and 0.17 g/l gelatin. Samples were heated for five minutes at 94° C. (denaturation of DNA), and cooled to room temperature. Two units of Taq polymerase were added to each sample. The reaction medium was heated at 55° C. for two minutes for annealing, then for two minutes at 70° C. for the primer directed DNA synthesis. This protocol was repeated for 30 cycles, resulting in a $10^6$ fold amplification.

d) Hybridization, (e) Detection and (f) Luminescence Detection were Performed as Described in EXAMPLE 9 g) Results

TABLE III shows that the XO dependent light emission from the different spots decreases as the number of base mismatches increases. The counting of each spot allows to clearly discriminate a single base mutation.

TABLE III

| Mismatches | 0 | 1 | 2 | 3 |
|---|---|---|---|---|
| photons/min | 80,000 | 35,000 | 7000 | 2000 |

Background: 1500 photons/min.

EXAMPLE 11

Dot Detection of Biotinylated Bovine Serum Albumin (BSA)

a) Preparation of XO-SA Conjugate
See EXAMPLE 9.

b) Preparation of Biotinylated BSA 80 mg of BSA are dissolved in 40 ml of pH 8.5, 50 mM Na Cl, 20 mM borate buffer. After addition of 8.0 mg biotin amino caproic acid N hydroxysuccinimide ester (Biotin X NHS) in 400 µl of anhydrous dimethylformamide, the solution is incubated at ambient temperature for 30 minutes and then dialyzed against phosphate buffered saline (pH 7.4, PBS)

c) Dot Assays

2 µl of serial dilutions of biotinylated BSA in PBS (concentrations ranging from 200 to 0.02 ng) were directly spotted onto strips of nitrocellulose filter (BA 85, Schleicher and Schuell). The nitrocellulose strips were allowed to air dry at ambient temperature and were blocked in PBS containing 2.5% BSA for at least one hour. They were then incubated in 2.5% BSA PBS containing XO-SA conjugate (2 µg/ml) for two hours at ambient temperature.

d) Luminescence Detection

The strips were washed 3×10 min with pH 8.4, 25 mM borate buffer containing 0.05% BSA and 0.01% Tween 80 and immersed in the luminescent reagent for at least five minutes. They were then placed between two sheets of Parafilm and exposed to a photographic film (Polaroid 412, 20 000 ASA) in a camera luminometer (Dynatech).

e) Results

Figure 12:
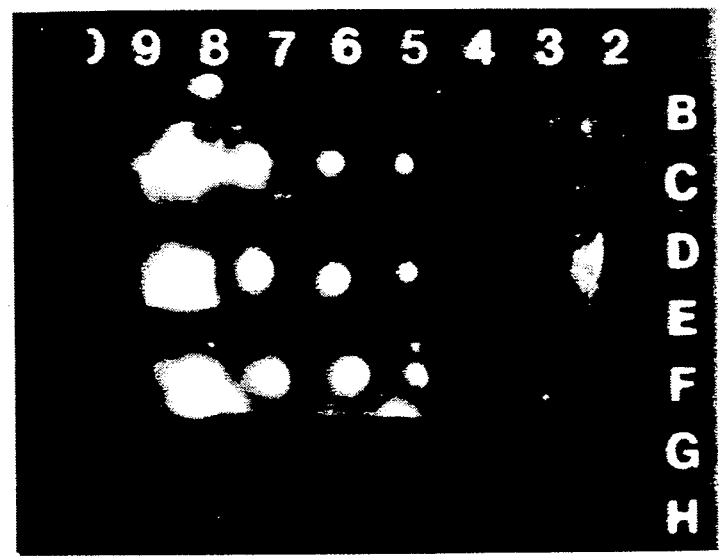

The results of the dot assay show that the XO label allows the detection of 20 pg of biotinylated BSA for an exposure time of 30 minutes (FIG. 12). Moreover, exposure periods can be repeatedly performed during at least 10 hours without loss of sensitivity.

Legend of FIG. 12

Dot assay of biotinylated bovine serum albumin using XO-SA conjugate. Serial dilutions of the test antigens were spotted.

EXAMPLE 12

Western Blotting of Human Urinary Proteins a) Preparation of XO-SA Conjugate
See EXAMPLE 9.

b) Biotinylation of Proteins

An aliquot (1 ml) of human urine containing 2 g/l of total proteins is desalted by gel filtration using a PD10 column eluted with PBS. The proteins are collected and biotinylated with biotin X NHS (w/w 20%). The reaction mixture is chromatographed with a PD10 column to eliminate the unreacted ester.

c) Western Blotting of Urinary Proteins

Serial dilutions of the biotinylated urinary proteins (20 µl, concentrations ranging from 250 to 0.4 ng) are separated on a 7.5% acrylamide mini-gel and electrophoretically transferred onto a sheet of nitrocellulose filter. The filter was blocked in PBS containing 2.5% BSA during at least one hour and then incubated in the same buffer containing XO-SA conjugate (2 µg/ml) for two hours at ambient temperature.

d) Luminescence Detection
See EXAMPLE 11.

e) Results

Figure 13A:
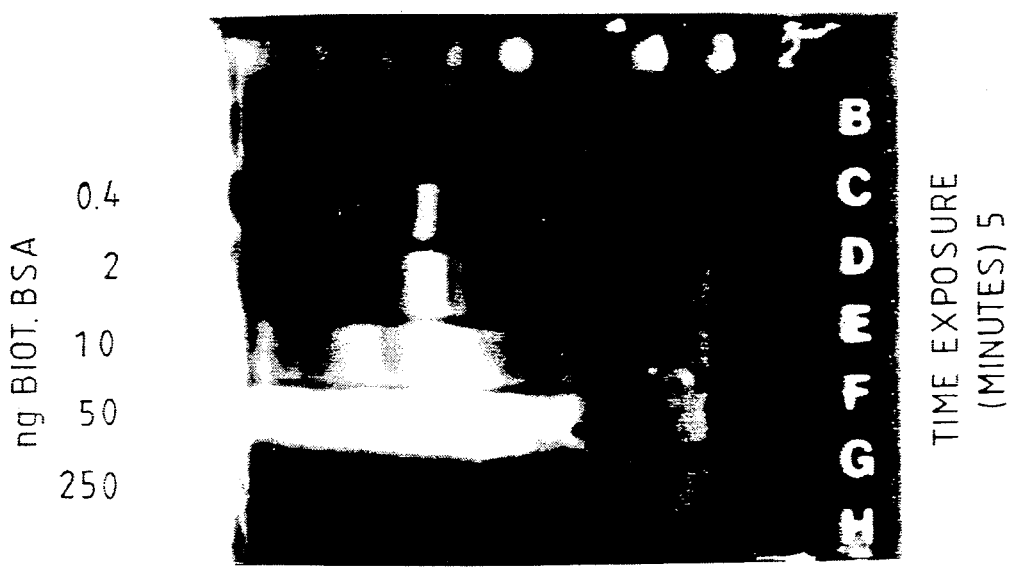
Figure 13B:
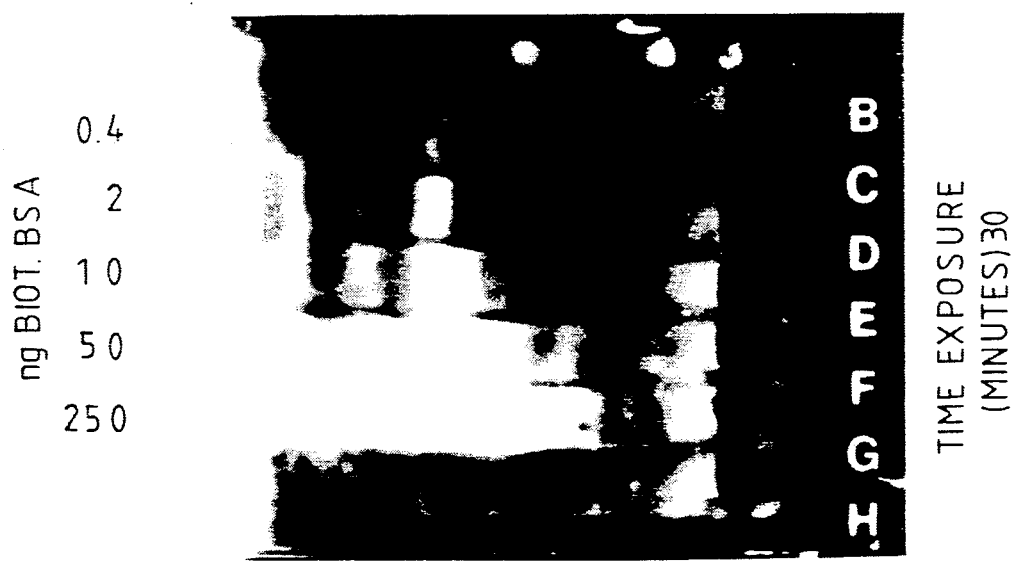

FIG. 13 shows the luminescent electrophoretic pattern obtained with various doses of total urinary proteins (250 to 0.4 ng). It appears that, for an exposure time of 30 minutes, the detection level is less than 0.4 ng. Exposure periods can be repeatedly performed during at least 10 hours without loss of sensitivity.

Legend of FIG. 13

Luminescent electrophoretic pattern obtained with serial dilutions of biotinylated urinary proteins. Serial dilutions of biotinylated total proteins were separated by SDS PAGE.

The foregoing description of the invention has been directed to particular embodiments for purposes of explanation and illustration. It will be apparent, however, to those skilled in the art that many modifications and changes in the processes of preparing and implementing the described embodiments can be made without departing from the essence of the invention. Applicant intends in the following claims to cover all equivalent modifications and variations as fall within the scope of the claims.

What is claimed is:

1. A kit for use in a chemiluminescent assay to detect an oligonucleotide analyte, comprising the following reagents in separate containers:
   a) a solid support for depositing the analyte;
   b) a conjugate of a complementary nucleotide binding partner to the analyte and an oxidase, said oxidase capable of producing both $H_2O_2$ and superoxide anion; and
   c) a signal reagent comprising at a pH ranging from about 9.5 to about 10.5, a substrate for said oxidase, a chemiluminescent reagent, and an iron EDTA enhancer.

2. The kit of claim I wherein the oxidase is xanthine oxidase, choline oxidase, fumarate oxidase or sarcosine oxidase.

3. The kit of claim 1 wherein the oxidase is xanthine oxidase.

4. The kit of claim 3 wherein the oxidase substrate is xanthine, hypoxanthine, acetaldehyde or purine.

5. The kit of claim 3 wherein the oxidase substrate is hypoxanthine.

6. The kit of claim 1 wherein the chemiluminescent reagent is luminol.

7. The kit of claim I wherein the signal reagent is maintained in barbital, carbonate or borate buffer.

8. The kit of claim I wherein the oxidase is xanthine oxidase, and wherein the signal reagent comprises hypoxanthine, luminol and iron EDTA enhancer.

9. A kit for use in a chemiluminescent assay to detect an oligonucleotide analyte, comprising the following reagents in separate containers:
   a) a solid support for depositing the analyte;
   b) a first conjugate of a biotin compound and a complementary nucleotide binding partner to the analyte;
   c) a second conjugate of an avidin compound and an oxidase, said oxidase capable of producing both $H_2O_2$ and superoxide anion; and
   d) a signal reagent comprising at a pH ranging from about 9.5 to about 10.5, a substrate for said oxidase, a chemiluminescent reagent, and an iron EDTA enhancer.

10. The kit of claim 9 wherein the oxidase is xanthine oxidase, choline oxidase, fumarate oxidase or sarcosine oxidase.

11. The kit of claim 9 wherein the oxidase is xanthine oxidase

12. The kit of claim 11 wherein the oxidase substrate is xanthine, hypoxanthine, acetaldehyde or purine.

13. The kit of claim 11 wherein the oxidase substrate is hypoxanthine.

14. The kit of claim 9 wherein the chemiluminescent reagent is luminol.

15. The kit of claim 9 wherein the signal reagent is maintained in barbital, carbonate or borate buffer.

16. The kit of claim 9 wherein the oxidase is xanthine oxidase, and wherein the signal reagent comprises hypoxanthine, luminol and iron EDTA enhancer.

17. A chemiluminescent method for detecting an oligonucleotide analyte in a sample by means of an oligonucleotide probe assay, wherein long term light emission for more than about 20 hours is produced in an oxidase-mediated reaction, the method comprising:
   a) providing a solid support for depositing said analyte;
   b) providing a tracer consisting of an oxidase coupled to a ligand which is a complementary nucleotide binding partner to the analyte, wherein said oxidase reacts with a substrate therefor to produce both $H_2O_2$ and superoxide anion;
   c) contacting said sample with said solid support and said tracer;
   d) separating unbound tracer from bound tracer by washing the contacted solid support;
   e) contacting the washed support with a signal reagent at a pH ranging from about 9.5 to about 10.5 comprising a substrate for the oxidase, a chemiluminescent reagent, and an iron EDTA complex enhancer, wherein the chemiluminescent reagent and the iron EDTA complex enhancer react in the oxidase-mediated reaction to produce emitted light; and
   f) measuring the emitted light to detect said analyte in the sample, wherein production of emitted light indicates presence of analyte.

18. The chemiluminescent method of claim 17 wherein the oxidase is xanthine oxidase, choline oxidase, sarcosine oxidase or fumarate oxidase.

19. The chemiluminescent method of claim 17 wherein the oxidase is xanthine oxidase.

20. The chemiluminescent method of claim 19 wherein the oxidase substrate is xanthine, hypoxanthine, acetaldehyde or purine.

21. The chemiluminescent method of claim 19 wherein the oxidase substrate is hypoxanthine.

22. The chemiluminescent method of claim 17 wherein the chemiluminescent reagent is luminol.

23. The chemiluminescent method of claim 17 wherein the pH is maintained by a barbital, carbonate or borate buffer.

24. The chemiluminescent method of claim 17 comprising a tracer of xanthine oxidase coupled to the ligand, and a signal reagent comprising hypoxanthine, luminol and iron EDTA complex.

25. The chemiluminescent method of claim 17 wherein the oxidase is coupled to the ligand by a direct covalent linkage or through a biotin-avidin linkage.

* * * * *